United States Patent [19]
Taylor, Jr. et al.

[11] Patent Number: 6,133,299
[45] Date of Patent: Oct. 17, 2000

[54] METHODS FOR TREATING NEURODEGENERATIVE DISEASES AND DISORDERS USING N-(2,6-DISUBSTITUTED AROMATIC)-N'-PYRIDINYL UREAS AND OTHER ANTICONVULSANT COMPOUNDS

[75] Inventors: Charles Price Taylor, Jr., Chelsea; Mark Lawrence Weber, Farmington Hills, both of Mich.

[73] Assignee: Warner-Lambert Company, Morris Plains, N.J.

[21] Appl. No.: 08/023,016

[22] Filed: Feb. 25, 1993

[51] Int. Cl.[7] ............................................. A61K 31/44
[52] U.S. Cl. ................................................. 514/353
[58] Field of Search .................................. 514/353

[56] References Cited

U.S. PATENT DOCUMENTS

| | | | |
|---|---|---|---|
| 2,409,754 | 10/1946 | Henze | 260/309.5 |
| 2,441,498 | 5/1948 | Löfgren | 260/562 |
| 2,948,718 | 8/1960 | Schindler | 260/239 |
| 4,405,644 | 9/1983 | Kabbe et al. | 424/322 |
| 4,602,017 | 7/1986 | Sawyer et al. | 514/242 |
| 4,629,731 | 12/1986 | Lobbestael et al. | 514/353 |

FOREIGN PATENT DOCUMENTS

| | | |
|---|---|---|
| 0124911 | 11/1984 | European Pat. Off. . |
| 2155856 | 5/1973 | France . |

OTHER PUBLICATIONS

*J. Am. Chem. Soc.*, 94:26 (1972), pp. 9219–9221, Y. Kishi, et al.
*TINS*, vol. 10, No. 7, 1987, pp. 294–298, J. A. Kemp, et al.
Merck Manual p. 1305–1313 (1982).
Stedman's Medical Dictionary, 24th Edition (1982) p. 1334.
Merck Manual pp. 1305–1313 (1982).

*Primary Examiner*—Marianne M. Cintins
*Attorney, Agent, or Firm*—Michael J. Atkins

[57] ABSTRACT

The instant invention is novel uses of known N-(2,6-disubstituted phenyl)-N'-3- and 4-pyridinyl ureas and pharmaceutically acceptable acid addition salts thereof. Such compounds as N-(2-chloro-6-methylphenyl)-N'-4-pyridinyl urea monohydrochloride or N-(2,3-dichlorophenyl)-N'-4-pyridinyl urea are used for treating neurodegenerative disorders, perinatal asphyxia, Alzheimer's disease, Huntington's disease, Parkinson's disease, and Amyotrophic Lateral Sclerosis. The instant invention is similar novel uses of known anticonvulsant compounds as ralitoline, phenytoin, lamotrigine, tetrodotoxin, lidocaine, and carbamazepine.

18 Claims, 4 Drawing Sheets

METHODS FOR TREATING NEURODEGENERATIVE DISEASES AND DISORDERS USING N-(2,6-DISUBSTITUTED AROMATIC)-N'-PYRIDINYL UREAS AND OTHER ANTICONVULSANT COMPOUNDS

BACKGROUND OF THE INVENTION

The present invention relates to novel therapeutic uses of a known compound, N-(2,6-disubstituted aromatic)-N'-pyridinyl ureas, its derivatives, and pharmaceutically acceptable salts. The present invention also relates to novel therapeutic uses of various other anticonvulsant drugs, their derivatives, and pharmaceutically acceptable salts. The present invention concerns a method for treating neurodegenerative diseases and disorders in a mammal in need of such treatment.

Such neurodegenerative diseases are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incidence (CVA) and includes acute thromboembolic stroke. Stroke includes both focal and global ischemia. Also included are transient cerebral ischemic attacks and other cerebrovascular problems accompanied by cerebral ischemia. A patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as those suffering from stroke for administration by methods of the present invention.

After ischemia of the brain in vivo many changes take place. There is a rapid loss of synaptic activity, a large shift in extracellular voltage, a release of the neurotransmitter glutamate, and a loss of ion homeostasis. The excess release of glutamate may be especially important in ischemic injury. Glutamate is an excitotoxin, meaning that overstimulation of glutamate receptor-linked channels allows excess calcium and sodium influx into neurons leading to neuronal death.

The overstimulation of receptors is thought to be involved in the etiology of several neurological disorders, i.e., epilepsy and cerebral ischemia. Evidence is also accumulating that the brain damage associated with anoxia, stroke, hypoglycemia, epilepsy, and perhaps neurodegenerative illnesses such as Alzheimer's or Huntington's diseases may be at least partially produced by excessive activation of N-methyl-D-aspartic acid (NMDA) receptors (Kemp J A, Foster A C, Wong E H F, *Trends in Neurosciences* 1987;10 (7):294–8).

The present invention employs the use of anticonvulsant compounds, such as the compounds of Formula I which are phenyl pyridinyl ureas as a method of blocking or delaying damage to neurons from conditions similar to ischemia. It is believed that by preventing neuronal damage, the compounds of Formula I, alone or together with a pharmaceutically acceptable carrier, can be used to treat neurological diseases such as Alzheimer's disease, Huntington's disease, Parkinson's disease, myotropic lateral sclerosis, and disorders such as stroke, head trauma, and asphyxia. The present invention is also directed to similar uses and methods of treatment employing other anticonvulsant compounds disclosed herein.

Various substituted phenyl pyridinyl ureas have been described but none having neuroprotective activity. For example, Bruce M I, Zwar J A, *Proc Roy Soc* (London), Sec. B. 165 (999), 1966;245–65 disclose many N-mono- and N,N'-disubstituted ureas having cytokinin activity. N-(3,4-dichlorophenyl)-N'-3- and 4-pyridinyl ureas show such activity whereas the corresponding 2,5-dichloro compounds were inactive. In general, the authors concluded that phenyl ring substitution enhanced activity with meta substituents providing highest activity and ortho substituents lowest activity.

German Patent Publication 2,928,485 also describes various ureas including N-(3-chloro-4-trifluoromethyl-phenyl)-N'-3- and 4-pyridinyl ureas as being useful for inhibiting lipid absorption.

French Patent Publication 2,155,856 teaches various 2-pyridinyl ureas including N-(3,4-dichlorophenyl)-N'-2-pyridinyl urea as having antiinflammatory and analgesic activity.

U.S. Pat. No. 4,629,731 covers the phenyl pyridinyl urea compounds of the instant invention, methods for preparing them, and their use as an anticonvulsant. The term convulsions is intended to mean the characteristic body movements which are associated with the group of chronic central nervous system disorders termed epilepsies. The patent is hereby incorporated by reference.

There is no disclosure in the above references to suggest the present invention's novel uses of compounds of U.S. Pat. No. 4,629,731 to treat neurodegenerative diseases and disorders in a mammal in need of such treatment.

SUMMARY OF THE INVENTION

The present invention relates to novel uses of anticonvulsant compounds such as the known compounds of the formula

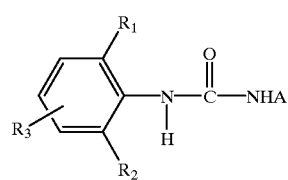

I wherein A is 3- or 4-pyridinyl; $R_1$ and $R_2$ are each independently halogen, lower alkyl, lower alkoxy, lower alkanoyl, lower alkoxycarbonyl, or nitro, and R3 is hydrogen, halogen, lower alkyl, lower alkoxy, lower alkanoyl, lower alkoxycarbonyl, or nitro, or a pharmaceutically acceptable acid addition salt thereof.

The present invention also relates to novel uses of various other anticonvulsant compounds such as ralitoline, phenytoin, lamotrigine, tetrodotoxin, lidocaine, and carbamazepine.

The present invention further includes novel uses of a pharmaceutical composition comprising a neuroprotective effective amount of a compound of Formula I or other anticonvulsant compounds together with a pharmaceutically acceptable carrier.

The novel uses of the instant invention concerns a method for treating neurodegenerative diseases or disorders in mammals suffering therefrom by administering to such mammals a neuroprotective effective amount of a compound of Formula I or the additionally disclosed anticonvulsants, or a compound of Formula I or the additionally disclosed anticonvulsants together with a pharmaceutically acceptable carrier, in unit dosage form.

DETAILED DESCRIPTION OF THE EMBODIMENTS

Figure 1A:
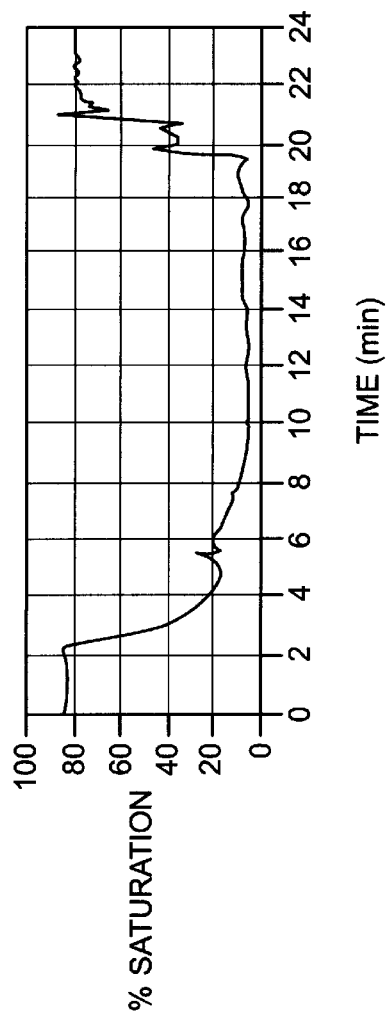
FIG. 1 are graphs reporting oxygen-tension measurements made with an oxygen-sensitive microelectrode in Example 3.

The term "halogen" as used herein in the definition of the compounds of the Formula I includes fluorine, chlorine, bromine, and iodine.

The term "lower" in reference to alkyl, alkoxy, alkanoyl, and alkoxycarbonyl pertains to a straight or branched carbon chain of from 1 to 4 carbon atoms, such as methyl, ethyl, propyl, isopropyl, n-butyl, sec-butyl, iso-butyl, or t-butyl.

The compounds of structural Formula I are basic in nature and form pharmaceutically acceptable salts with both organic and inorganic acids. Examples of such acids are acetic, hydrochloric, phosphoric, nitric, sulfuric, fumaric, citric, maleic, malic, and the like. The salts are prepared by contacting the free base form of the pyridinyl urea with an equivalent amount of the desired acid in the conventional manner. The free base forms may be regenerated by treating the salt form with a base. For example, dilute aqueous basic solutions may be utilized. Dilute aqueous sodium hydroxide, sodium carbonate, or ammonia are suitable for this purpose. The free base forms differ from their respective salt forms somewhat in certain physical properties such as solubility in polar solvents, but the salts are otherwise equivalent to their respective free base forms for purposes of the invention.

The compounds of the invention of Formula I can exist in unsolvated as well as solvated forms, including hydrated forms. In general, the solvated forms, with pharmaceutically acceptable solvents such as water, ethanol, and the like are equivalent to the unsolvated forms for purposes of the invention.

A preferred embodiment of the compound of the Formula I employed as a neuroprotective agent is where $R_3$ is hydrogen or a pharmaceutically acceptable acid addition salt thereof.

Another preferred embodiment of the compound of the Formula I is where $R_1$ and $R_2$ are each independently halogen or lower alkyl, or a pharmaceutically acceptable acid addition salt thereof.

Still another preferred embodiment of the compound of Formula I is where $R_1$ and $R_2$ are each independently chlorine or methyl.

Particular embodiments are the following compounds:
N-(2-chloro-6-methylphenyl)-N'-4-pyridinyl urea monohydrochloride;
N-(2,3-dichlorophenyl)-N'-4-pyridinyl urea;
N-(2,6-dichlorophenyl)-N'-4-pyridinyl urea;
N-(2,6-dichlorophenyl)-N'-3-pyridinyl urea;
N-(2,6-dimethylphenyl)-N'-4-pyridinyl urea;
N-(2,6-dimethylphenyl)-N'-3-pyridinyl urea;
N-(2-chloro-6-methylphenyl)-N'-4-pyridinyl urea;
N-(2-chloro-6-methylphenyl)-N'-3-pyridinyl urea;
N-(2,6-diethylphenyl)-N'-4-pyridinyl urea;
N-(2,6-diethylphenyl)-N'-3-pyridinyl urea;
N-(2,6-dimethyl-4-bromophenyl)-N'-4-pyridinyl urea;
N-(2,6-dimethyl-4-bromophenyl)-N'-3-pyridinyl urea;
N-(2,4,6-trimethylphenyl)-N'-4-pyridinyl urea;
N-(2,4,6-trimethylphenyl)-N'-3-pyridinyl urea;
N-(2,4,6-trichlorophenyl)-N'-4-pyridinyl urea;
N-(2,4,6-trichlorophenyl)-N'-3-pyridinyl urea;
or a pharmaceutically acceptable acid addition salt thereof.

The compounds of Formula I may be prepared by reacting an isocyanate of the formula

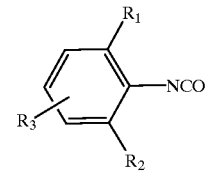

II with an equimolar amount of 3- or 4-aminopyridine in an inert solvent, such as tetrahydrofuran, dioxane, and the like, at elevated temperatures, such as at the boiling point of the solvent used.

The starting materials such as the various isocyanates are known and can be purchased commercially or synthesized by known methods.

The additional compounds, which are anticonvulsant compounds and can be used as agents for treating neurogenerative diseases or disorders as heretofore discussed, include ralitoline, phenytoin, lamotrigine, tetrodotoxin, lidocaine, and carbamazepine. The methods for making and administering each of these compounds are known to those skilled in the art and can be shown respectively by reference to the following publications: European Patent 124,911, U.S. Pat. Nos. 2,409,754 and 4,602,017, Kishi et al, *Am Chem Soc* 1972;94:9219, U.S. Pat. Nos. 2,441,498 and 2,948,718. As it will be illustrated at a later point, each of these compounds have been shown in vitro to have neuroprotective capabilities.

It should be understood that the present invention is not limited to the use of the anticonvulsant compounds disclosed herein. Similar compounds which prevent irreversible neuronal damage from conditions similar to ischemia are also included in the present invention. In addition, anticonvulsant compounds that bind to sodium channels or that cause a voltage-dependent block to sodium currents or that modulate ion channels without simply blocking them are also included in the present invention.

The compounds of structural Formula I, and the additionally disclosed anticonvulsant compounds, can be prepared and administered in a wide variety of oral and parenteral dosage forms. The compounds of structural Formula I or the other disclosed anticonvulsant compounds can also be administered intravenously. For example, a useful oral dosage is between 50 and 5000 mg, a useful parenteral dosage is between 50 and 2000 mg, and a useful intravenous dosage is between 10 and 1000 mg.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compounds of the present invention. In the tablet the active compound is mixed with carrier having the necessary binding properties in suitable proportions and compacted in the shape and size desired. The powders and tablets preferably contain from 5% to 10% to about 70% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example, water or water-propylene glycol solutions may be mentioned for parenteral injections. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents. Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 10 mg to 1000 mg according to the particular application and the potency of the active ingredient.

In therapeutic use as agents for treating neurodegenerative diseases or disorders, the compounds utilized in the pharmaceutical methods of this invention are administered at the initial dosage of about 1 mg/kg to about 30 mg/kg daily. A daily dose range of about 3 mg/kg to about 10 mg/kg is preferred. The dosages, however, may be varied depending upon the requirements of the patient, the severity of the condition being treated, and the compound being employed. Determination of the proper dosage for the particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The advantages of using the compounds of the instant invention include the relatively nontoxic nature of the compound, the ease of preparation, the fact that the compound is well tolerated, and the ease of administration of the drug.

The following nonlimiting examples illustrate the preferred methods for preparing and using the compounds of the invention.

EXAMPLE 1

N-(2,6-Dichlorophenyl)-N'-4-pyridinyl urea

A solution of 4.7 g (0.05 mol) of 4-aminopyridine in 300 mL of anhydrous tetrahydrofuran was treated with 9.4 g (0.05 mol) of 2,6-dichlorophenylisocyanate. The solution was heated at reflux for 24 hours, cooled, and concentrated in vacuo to a solid. Recrystallization from aqueous ethanol afforded the crystalline product, mp 217–219° C.

EXAMPLE 2

In a similar manner as described in Example 1, the following compounds were prepared by reacting the appropriate isocyanate with 3- or 4-aminopyridine:

N-(2,6-dichlorophenyl)-N'-3-pyridinyl urea, mp 225–227° C.;

N-(2,6-dimethylphenyl)-N'-3-pyridinyl urea, mp 190–192° C.;

N-(2,6-dimethylphenyl)-N'-4-pyridinyl urea, mp 187–188° C.;

N-(2,6-diethylphenyl)-N'-3-pyridinyl urea, mp 196–197° C.;

N-(2,6-diethylphenyl)-N'-4-pyridinyl urea, mp 178–180° C.;

N-(2-chloro-6-methylphenyl)-N'-3-pyridinyl urea, mp 246–247° C.; and

N-(2-chloro-6-methylphenyl)-N'-4-pyridinyl urea, mp 210–212° C.

EXAMPLE 3

An in vitro model with rat hippocampal brain slices exposed to hypoxia-hypoglycemia was used to simulate ischemia. Neuroprotection was measured by the recovery of excitatory postsynaptic potentials after reoxygenation.

Oxygen tension was measured in superfusing solution and in slice tissue using polarized glass-insulated carbon fiber electrodes according to the methods of Jiang, et al (*Brain Res* 1991;568:159–64). The polarographic potential was −750 mV and the carbon fiber sensing element was 8 $\mu$m in diameter.

Young male Wistar rats (150 to 250 g) were anesthetized with ketamine (200 mg/kg IP) and ether and were perfused transcardially with cold, oxygenated, low sodium-containing physiological buffer solution (252 mM sucrose, 3.5 mM KCl, 1.0 mM $MgSO_4$, 20 mM $CaC_1$, 26 mM $NaHCO_3$, 1.25 mM $NaH_2PO_4$, and 10 mM glucose) with 50 $\mu$M ketamine added. Brains were removed and hippocampi carefully excised. Hippocampi were sliced transversely at 450 $\mu$m and transferred into cold (4° C.) low-sodium buffer solution gassed with 95% $O_2$, 5% $CO_2$ at 31° C. After 45 minutes slices were transferred to oxygenated normal physiological solution (126 mM NaCl, 3.5 mM KCl, 1.0 mM $MgSO_4$, 2.0 mM $CaCl_2$, 20 mM $NaHCO_3$, 1.25 mM $NaH_2PO_4$, and 10 mM glucose) at 31° C. for at least 1 hour before experiments began. After preincubation, slices were transferred to a heated (36° C.), gassed incubation chamber where they were continuously superfused with gassed normal physiological solution. Evoked extracellular synaptic potentials (EPSPs) were obtained using glass micropipettes placed approximately 100 μm into the slice. Electrical stimulation was applied once per minute to the stratum radiatum by insulated paired nichrome wires (60 μm diameter). Stimuli consisted of 150 μA pulses lasting 0.4 msec. The 150 μA stimulus usually gave nearly a maximal EPSP (excitatory postsynaptic potential) amplitude. Data from a slice were used only if EPSP amplitude was greater than 2.0 mV before hypoxia-hypoglycemia.

Evoked potentials were recorded and analyzed with a digital computer interface. Experiments were started by recording for several minutes under normal conditions (95% $O_2$, 5% $CO_2$, 10 mM glucose). Then drug was added to the superfusion solution (or normal solution was continued in control experiments). After 10 minutes of drug superfusion, hypoxia-hypoglycemia was induced by switching to superfusion solution containing added drug with low glucose (2 mM) that was equilibrated with 95% $N_2$ and 5% $CO_2$. At the same time the slice chamber gas was switched to 95% $N_2$ and 5% $CO_2$. Hypoxia-hypoglycemia was continued for 12 minutes. After 12 minutes, 95% $O_2$ and 10 mM glucose were returned to the slices and the superfusing solution. Following 15 minutes of reoxygenation, the experiment was ended. EPSPs were considered recovered if they returned to at least half of their original amplitude. The percentage of slices with recovered EPSPs were calculated for each condition.

Oxygen-Tension Measurements

Oxygen tension was measured in medium flowing through the experimental chamber. When the medium, as well as the gas within the chamber was switched from 95% oxygen to 95% nitrogen (carbon dioxide constant at 5%). Results in FIG. 1A show that oxygen tension decreased from 95% to approximately 20% of saturation within 1 minute and then reached a plateau of approximately 5% after 4 minutes. Recovery of oxygen tension in the medium upon reoxygenation was rapid, with complete recovery within 30 to 40 seconds.

Figure 1B:
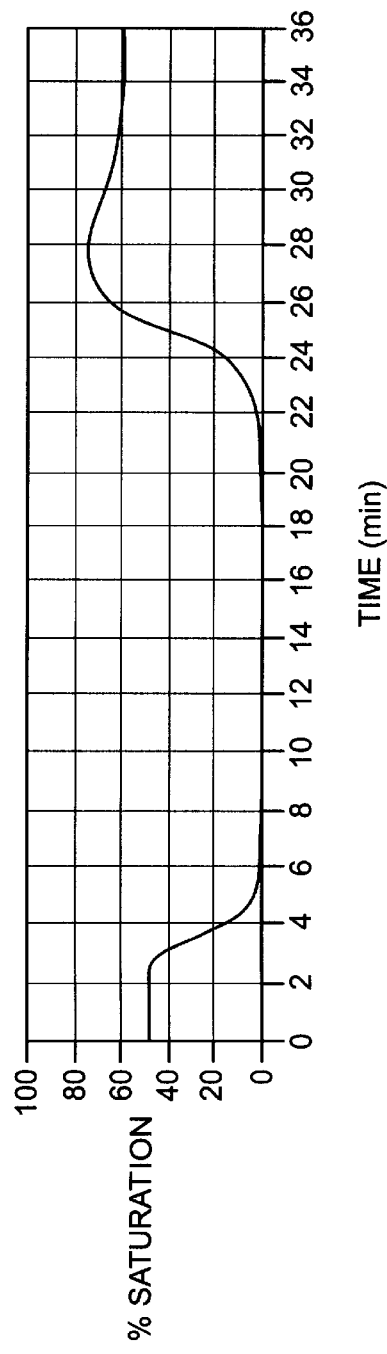

Oxygen tension was also measured approximately 100 μm deep within hippocampal slice tissue, a depth similar to that used for microelectrode voltage recordings. In stratum pyramidale, oxygen tension under resting conditions was 50% to 65% of saturation as shown in FIG. 1B. Oxygen tension in tissue is lower than in bathing medium, presumably because of oxygen utilization by the tissue in agreement with previous studies. After switching to hypoxic medium, oxygen tension in tissue decreased more rapidly and completely than in superfusate, reaching less than 4% of saturation within 1 minute and falling to undetectable low levels within 2 minutes. Despite the rapid fall in oxygen tension, synaptic potentials and population spikes in the CA1 cell body area were seen for at least 3.5 minutes after the start of hypoxia (a typical result in these experiments). Oxygenated medium was reapplied 9 minutes after the start of hypoxia. Oxygen tension in tissue returned to approximately 75t of saturation over 4 to 5 minutes and then finally reached a resting level of approximately 55%. In this experiment as in many others without drug treatment, synaptic potentials never returned following more than 20 minutes of reoxygenation (see below). The time course and extent of changes in tissue oxygen tension were similar in two other experiments with a shorter duration of hypoxia that allowed complete recovery of synaptic potentials (data not shown).

Synaptic Potential Measurement

Excitatory synaptic potential (EPSP) amplitude was measured before and during drug treatment in the 10-minute period preceding reduced oxygen and glucose. None of the drug treatments altered synaptic potentials before hypoxia (data not shown). Without addition of drug (in control experiments), reduction of oxygen and glucose caused a rapid loss of synaptic potentials in each of 20 slices.

TABLE 1

Table Shows Effects of Different Concentrations of N-(2-chloro-6-methylphenyl)-N'-4-pyridinyl Urea on Recovery of Synaptic Activity (EPSP) in Hippocampal Slices After Hypoxia-hypoglycemia

| Compound Tested | Concentration (μM) | Number Slices Recovered[b]/ Number Slices Tested | p-Value vs Control[a] |
|---|---|---|---|
| Controls | — | 1/20 | — |
| Test drug | 0.5 | 0/8 | NS |
| Test drug | 2 | 3/8 | 0.058 |
| Test drug | 20 | 9/10* | <0.00001 |

*Significantly different than controls ($p < 0.05$)
NS = Not significantly different than controls ($p > 0.1$)
[a]p-Value by Fisher's exact test (two-tailed) compared to controls
[b]Slices with ≥50% EPSP amplitude recovery after reoxygenation After 12 minutes of reduced oxygen and glucose and 15 minutes of recovery, EPSP amplitude was measured again. EPSP amplitude was scored as recovered if more than half of the initial value was recorded. Table 1 and FIG. 2 show that treatment with N-(2-chloro-6-methylphenyl)-N'-4-pyridinyl urea increased the percentage of slices that recovered EPSPs from approximately 5% (control) to 37% at 2 μM and 90% at a concentration of 20 μM ($p<0.00001$ by Fisher's exact test).

Figure 2:
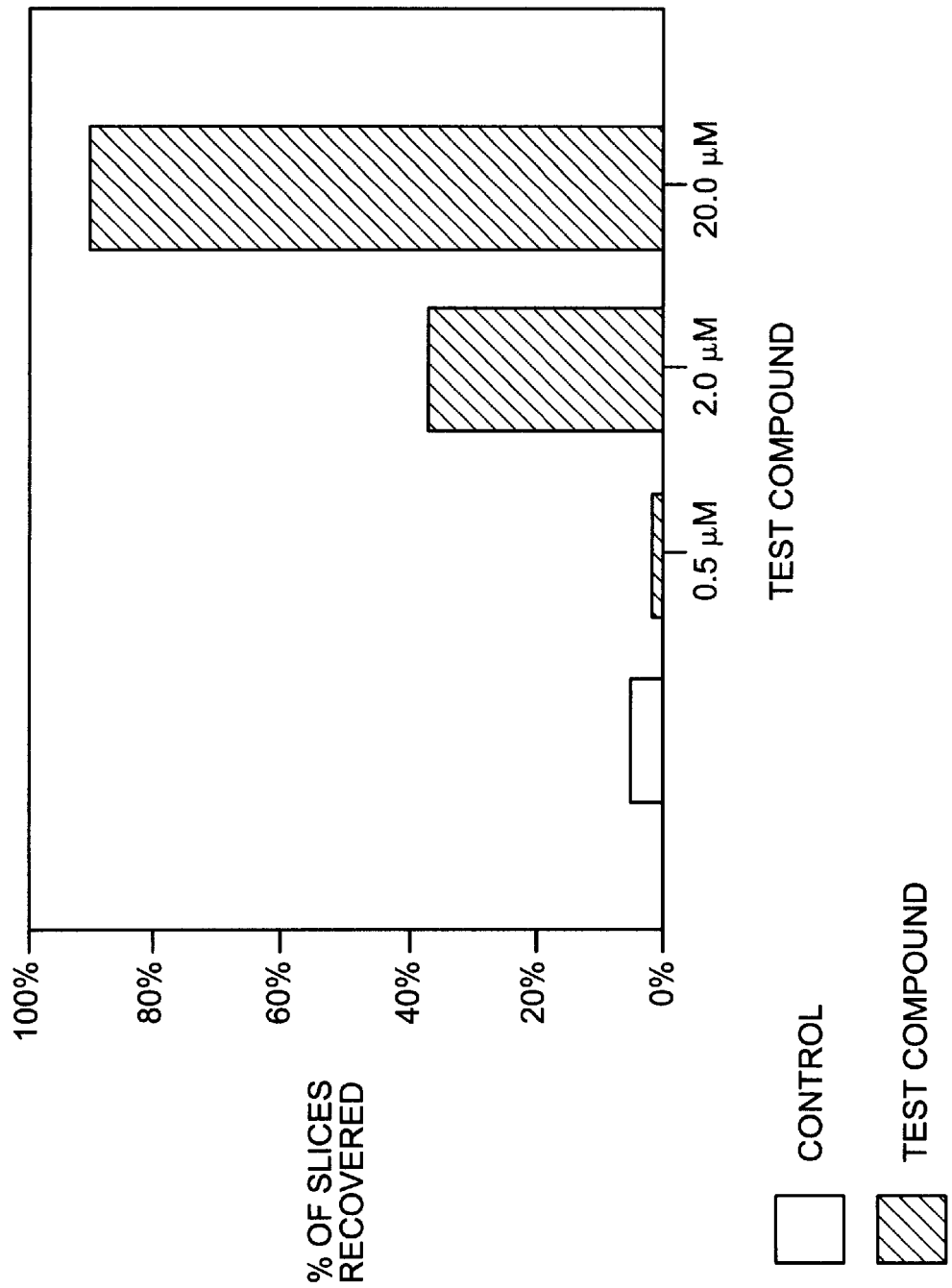
FIG. 2 is a graph reporting that the percentage of slices that recovered at least half of their Prehypoxic-Hypoglycemic Synaptic Potential Amplitude increased with increasing concentrations of a compound of Formula I.

In FIG. 2, drug concentrations are listed below each column. The 20 μM concentration of N-(2-chloro-6-methylphenyl)-N'-4-pyridinyl urea gave almost complete protection from loss of EPSPs. [20 μM concentration—$p<0.01$ compared to control slices by Fisher's exact test (two-tailed); 2 μM concentration—$p<0.05$].

In addition to increasing the number of slices that reached a 50% criterion for recovery of EPSPs, treatment with N-(2-chloro-6-methylphenyl)-N'-4-pyridinyl urea significantly increased the mean EPSP amplitude after hypoxia as a percentage of the control. This was also a concentration-related effect that was near significance at a concentration of 2 μM and was significant with a high degree of confidence at 20 μM.

Figure 3:
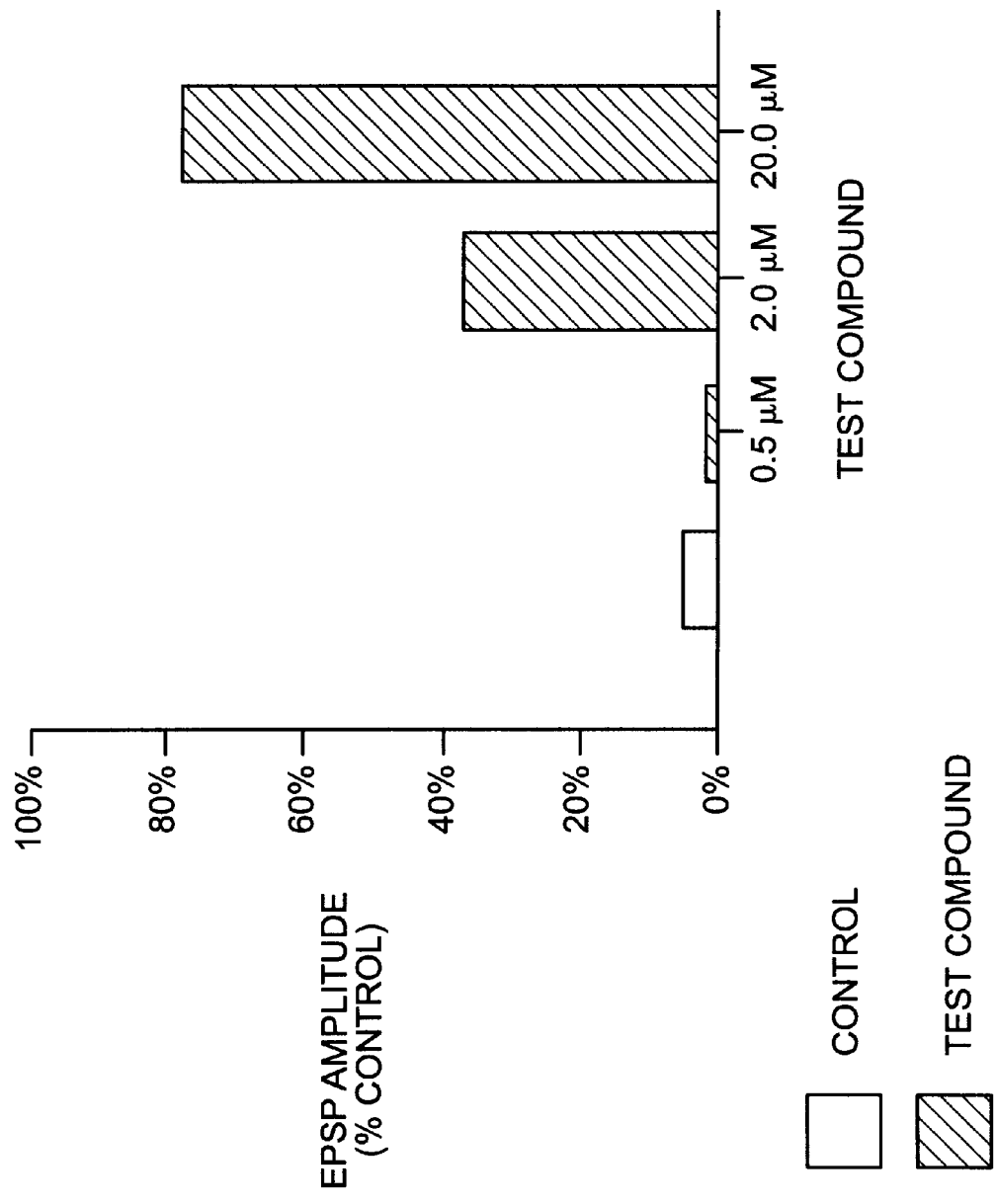
FIG. 3 are graphs of the mean EPSP Amplitudes at the end of the experiments conducted in Example 3.

In FIG. 3, use of N-(2-chloro-6-methylphenyl)-N'-4-pyridinyl urea increased EPSP amplitude following hypoxia in a concentration-dependent manner. Standard error of the mean and p-values for significance compared to controls for concentrations at 2 μM and 20 μM were as follows(Student's two-tailed t-test): 2 μM—$p \leq 0.07$; 20 μM—$p \leq 0.0002$. As indicated in the graph, the use of 20 μM of N-(2-chloro-6-methylphenyl)-N'-4-pyridinyl urea caused an almost complete recovery of EPSPs.

Treatment with 0.5 μM of N-(2-chloro-6-methyl-phenyl)-N'-4-pyridinyl urea resulted in changes from hypoxia that were not different from control treatments with no drug present.

Treatment with the two higher concentrations of N-(2-chloro-6-methylphenyl)-N'-4-pyridinyl urea provides significant protection of hippocampal slices from irreversible loss of synaptic potentials after brief application of conditions that mimic ischemia in vitro. Previous studies (Rock D M, McLean M J, Macdonald R L, et al, *Epilepsy Res* 1991;8:197–203) show that N-(2-chloro-6-methylphenyl)-N'-4-pyridinyl urea modulates voltage-dependent sodium channels of nerve cell membranes, and the inventors have determined that this modulation provides protection from hypoxia. A previous study with slices also shows that tetrodotoxin, a very selective sodium channel blocker, delays negative shifts from hypoxia. Also, phenytoin, another anticonvulsant, has shown effects preventing neuronal damage from ischemia both in vitro and in vivo. The results showed that treatment with N-(2-chloro-6-methylphenyl)-N'-4-pyridinyl urea improves recovery of EPSPs at both 2 µM and 20 µM with the 20 µM concentration giving almost complete protection (9 out of 10 slices recovered).

N-(2-chloro-6-methylphenyl)-N'-4-pyridinyl urea is a modulator of neuronal voltage-gated sodium ion channels. However, it is important to point out that none of the concentrations tested reduced EPSP or presynaptic action potential amplitude. Thus, neuroprotection was obtained by modulating ion channels without simply blocking them. These results suggest that neuroprotection in vivo might be obtained at drug doses that would not greatly alter normal neuronal function.

Although the results with irreversible loss of EPSPs do not directly demonstrate that the test drug prevents ischemic neuronal cell loss, this hypothesis can be tested using histological or biochemical techniques. One hypothesis for the neuroprotective action of this compound is that it blocks neuronal hyperactivity or reduces sodium influx (by modulating sodium channels) and therefore reduces energy demand and preserves ion homeostasis, preventing depolarization similar to that of spreading depression. A similar hypothesis has been advanced for the protection of white matter from hypoxic injury by local anesthetic compounds. Also, a recent report suggests that prevention of spreading depression-like events in vivo underlie the action of certain drugs that prevent tissue infarction from focal ischemia in rats (Gill, et al, *J Neuro* 1992;67:236–40).

In conclusion, this study provides evidence that the test drug or similar sodium ion channel modulating drugs prevent neuronal damage from ischemia.

EXAMPLE 4

This study was identical in design to Example 3 except that during the hypoxic period of 12 minutes, glucose was reduced from 10 mM to 2 mM rather than from 10 mM to zero as in Example 3.

Synaptic Potential Measurement

Without addition of drugs, hypoxia/hypoglycemia caused a rapid loss of synaptic potentials in each of 36 control slices. None of the drug treatments altered synaptic potentials at the concentrations used (data not shown). However, lidocaine reversibly reduced both presynaptic action potential and EPSPs at a concentration of 500 µM (data not shown).

TABLE 2

Table Shows Effects of the Drugs Known to Interact With Voltage-dependent Sodium Channels on Recovery of Synaptic Activity (EPSP) in Hippocampal Slices After Hypoxia-hypoglycemia

| Compound Tested | Concentration (µM) | Number Slices Recovered[a]/ Number Slices Tested | p-Value vs Control[b] |
| --- | --- | --- | --- |
| Controls | — | 0/36 | — |
| Phenytoin | 5 | 0/8 (NS) | >0.1 |
| Phenytoin | 20 | 5/12* | 0.0005 |
| Phenytoin | 50 | 3/9* | 0.0059 |
| Carbamazepine | 20 | 2/9* | 0.036 |
| Carbamazepine | 50 | 4/10* | 0.0013 |
| Lidocaine | 50 | 5/9* | 0.0001 |
| Lidocaine | 200 | 9/10* | <0.00001 |
| Verapamil | 1.0 | 3/8* | 0.0042 |
| Verapamil | 10 | 5/9* | 0.0001 |
| Nimodipine | 1.0 | 1/9 (NS) | >0.1 |

[a]Slices with ≧50% EPSP amplitude recovery after reoxygenation
[b]p-Value by Fisher's exact test (two-tailed) compared to controls
*Significantly different than controls (p < 0.05)
NS = Not significantly different than controls (p > 0.1)

Table 2 summarizes data obtained with drug treatments. Seven to 20 slices were recorded in each drug condition and 36 control slices were studied interspersed from time to time over the 4-month period of experiments.

Figure 4:
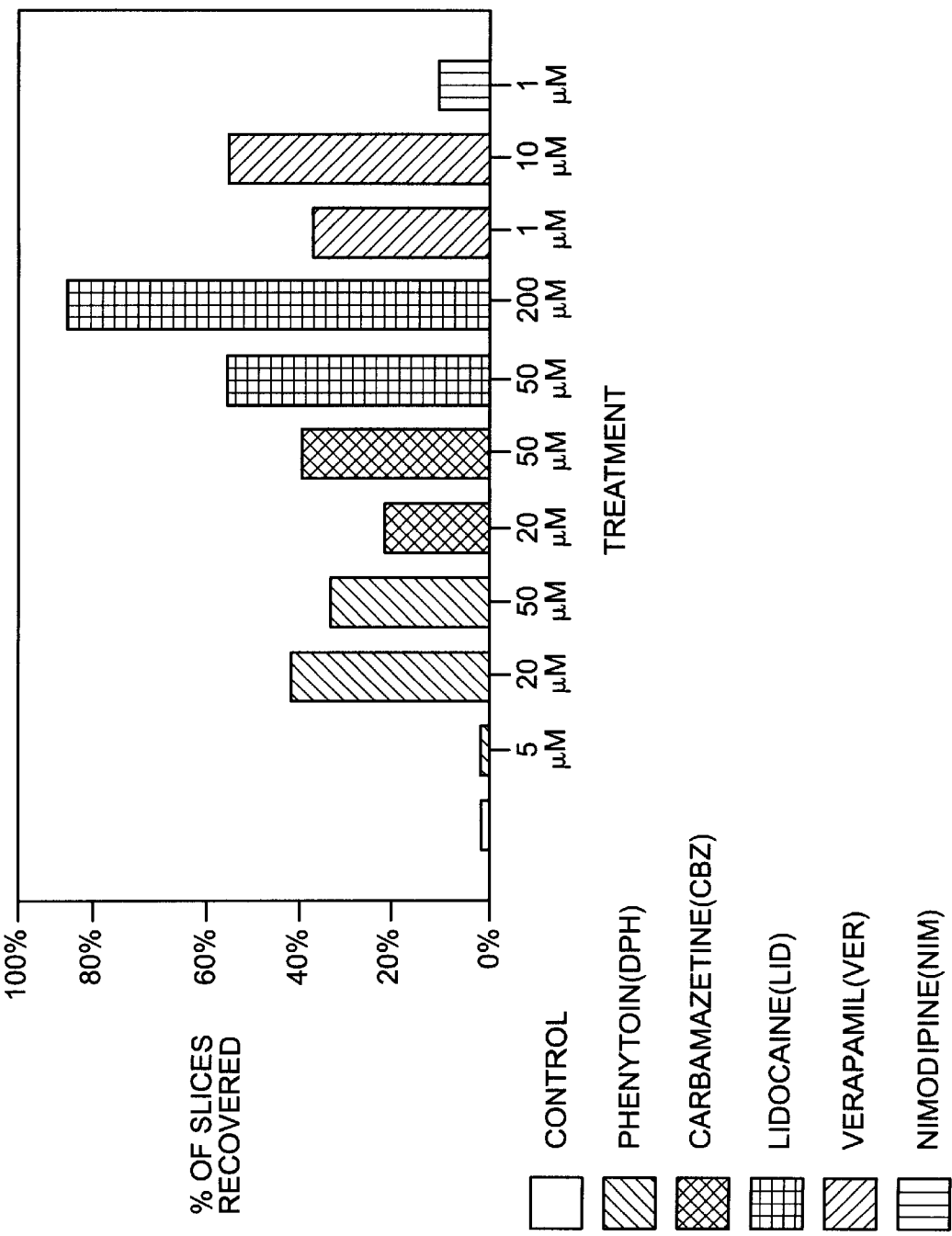
FIG. 4 is a graph indicating that the percentage of slices that recovered at least half of their Prehypoxic-Hypoglycemic Synaptic Potential Amplitude varied with drug treatments.

Drug treatment enhanced recovery of EPSPs (especially with lidocaine, phenytoin, and verapamil). FIG. 4 shows the significance of EPSP recovery for drug treatment in comparison to controls.

Standard error of the mean p-values for significance compared to controls for the following were found (students' two-tailed t-test):
20 µM phenytoin—p<0.01
50 µM phenytoin—p<0.01
50 µM carbamazepine—p<0.01
50 µM lidocaine—p<0.01
200 µM lidocaine—p<0.01
20 µM carbamazepine—p<0.05

Drug intervention with four of the five drugs during hypoxia-hypoglycemia provides significant neuroprotection. All four drugs modulate sodium channels. A previous study with slices also shows that tetrodotoxin, a very selective sodium channel blocker delays loss of ion homeostasis from hypoxia. Results with phenytoin are similar to those with other models of ischemia in vitro and in vivo with models of focal ischemia and global ischemia. Lidocaine treatment improves recovery of EPSPs at both concentrations tested, with 200 µM concentration giving almost complete protection (9/10 slices recovered). Although the use of lidocaine for ischemia in vivo is limited by its peripheral hypotensive effects, one study reports that brain damage from global ischemia in rabbits is reduced by lidocaine and another recent study reports neuroprotection by local anesthetics in a model of white matter ischemia.

Each of the drugs in our study are modulators of neuronal voltage-gated ion channels. However, it is important to point out that none of the drugs reduced EPSP or presynaptic action potential amplitude at the concentrations used. Thus, neuroprotection was obtained by modulating ion channels without simply blocking them. These results suggest that neuroprotection in vivo might be obtained at drug doses that would not greatly alter normal neuronal function.

Several of these agents modulate calcium channels as well as sodium channels. Phenytoin blocks a variety of calcium channels at concentrations similar to those tested here while carbamazepine and lidocaine are thought to be more selective for sodium channels. In addition to modulating sodium channels, verapamil is a widely studied blocker of L-type calcium channels. However, verapamil prevented ischemic damage at 10 µM but not at 1 µM. The 10 µM concentration is supermaximal for blocking L-type channels but is near the threshold for sodium channel. These results suggest that the neuroprotective action of verapamil is caused by action at sodium channels and not calcium channels. This notion also is supported by results with 1 μM nimodipine which failed to prevent loss of EPSPs (nimodipine interacts with sodium channels at concentrations greater than 10 μM). Tetrodotoxin, a highly selective blocker of neuronal sodium channels, previously has been reported to reduce neuronal damage from global ischemia.

Although the results with irreversible loss of EPSPs do not directly demonstrate that sodium channel modulators prevent ischemic neuronal cell loss, this hypothesis can be tested using histological techniques. One hypothesis for the neuroprotective action of these compounds is that they block neuronal hyperactivity or reduce sodium influx (by modulating sodium channels) and therefore reduce energy demand and preserve ion homeostasis.

In conclusion, this study provides evidence that these or similar ion channel modulating drugs prevent neuronal damage from ischemia.

EXAMPLE 5

An assay was conducted to compare the inhibitory action of various compounds which are the subject of the present invention. The assay measured the oxygen deprivation-induced neuronal cell death from various cortical cultures. The results of the assay are provided in Table 3. Lactate dehydrogenase (LDH) is a cytosolic enzyme that is only present in the extracellular medium if cell membranes rupture, indicating cell death. Therefore, LDH release into the culture medium is a convenient assay of cell death. The results of Table 3 indicate that each of the compounds tested decreased neuronal cell death from hypoxia in vitro. These results suggest that each of the compounds reduce damage from brain ischemia, stroke, or neurodegenerative diseases.

Primary Culture Preparation

The uteri of Sprague Dawley rats in their 18th day of fetal gestation were removed under halothane anesthesia and placed in a chilled bath of magnesium and calcium-free Hank's balanced salt solution (HBSS). Cortical brain hemispheres were removed from individual fetuses and digested in 0.1% trypsin in HBSS for 15 minutes at room temperature. Digested tissue was washed three times with HBSS then dissociated into a single cell suspension by trituration with a glass pipette. Using a growth medium containing 42% Delbecco's modified Eagle's medium with 42% HAM F12 nutrient supplement, 10% heat inactivated horse serum, and 6t heat inactivated fetal calf serum (10/6 DME/F12), cell density was adjusted to one cortical hemisphere per 10 mL of triturated suspension. One hundred microliters of this cell suspension was pipetted into individual wells of 96-well tissue culture plates previously coated with poly-L-lysine, then stored in a humidified incubator (37° C., 3% $CO_2$). Glial cell growth was stopped by the addition of 100 μL of 45% DME, 45% HAM F12, and 10% Horse serum (10/0 DME/F12) containing 15 μg/mL of 5-fluoro-2-deoxyuridine and 35 μg/mL of uridine, 3 days after the initial plating. Cultures were fed at 2- or 3-day intervals thereafter by replacing 100 μL of spent medium with an identical volume of fresh 10/0 DME/F12.

Experimental Protocol

Sixteen-day-old cultures were prepared for experiments by removing growth medium from each culture well and rinsing once with 250 μL of $Mg^{++}$-free HBSS containing 1.8 mM $Ca^{++}$ and 1 g/L D-glucose (0 Mg-HBSS) Control and test agent solutions, prepared using 0 Mg-HBSS medium, were dispensed in 50 μL aliquots into individual test wells (Total volume/well=50 μL). All liquid medium preparations to this point were equilibrated with 95% oxygen, 5% $CO_2$. Plates were placed into a 37° C., humidified, triple-gas incubator with $O_2$ and $CO_2$ levels maintained at 1% and 10%, respectively. Plates were removed after 7.5 hours of oxygen deprivation and restored to normoxic conditions (20% $O_2$/10% $CO_2$, 37° C.) following a 50 μL addition to each well of appropriate control or test agent solutions containing 1.8 mM $Ca^{++}$, 1.6 mM $Mg^{++}$, and 7.0 g/L D-glucose. Final medium concentrations of 1.8 mM $Ca^{++}$, 0.8 mM $Mg^{++}$, and 4 g/L D-glucose were present during the reoxygenation period.

Medium concentrations of lactate dehydrogenase (LDH), a cytosolic enzyme normally retained by cells but released upon cell death, were determined for each well following an additional 16.5-hour normoxic exposure period. Individual 25 μL medium specimens were collected from each well and placed into wells of a clean 96-well microtiter plate containing 225 μL of 0.1 M $KPO_4$ buffer (pH=7.5 at 25° C.) and 30 μg NADH (reduced α-nicotinamide adenine dinucleotide). After 10-minute incubation at 37° C., 30 μL of 2.4 mM sodium pyruvate was added to each well and plates were gently shaken to mix solution. Plates were immediately placed into a Multiscan MCC/340 plate reader and scanned for fluorescence (excitation at 340 nM) for 1 minute at 5-second intervals. A kinetic analysis of the change in medium absorbance resulting from shifts in NADH concentrations was used, in combination with factors to correct for temperature, light path, and volume adjustments to determine medium LDH concentrations (IU/mL). Normoxic control baseline LDH levels were subtracted from both hypoxic control and test agent values prior to determining test agent effectiveness in preventing oxygen deprivation-induced injury.

TABLE 3

Hypoxia-Induced Lactate Dehydrogenase Release (Cell Injury) in Neuronal/Glial Cortical Cultures

| Test Group | | LDH Release | % Inh[a] |
|---|---|---|---|
| Normoxic control | | 74 ± 4 | 100% |
| Hypoxic Control | | 163 ± 11 | 0% |
| CPP | 100 μM | 80 ± 8 | 93% |
| TTX | 3 μM | 81 ± 5 | 92% |
| Lamotrigine | 30 μM | 102 ± 16 | 68% |
| | 100 μM | 89 ± 6 | 83% |
| Phenytoin | 30 μM | 93 ± 6 | 78% |
| | 100 μM | 90 ± 3 | 82% |
| N-(2,6-dichlorophenyl)-N'-4-pyridinyl urea | 30 μM | 107 ± 8 | 62% |
| | 100 μM | 84 ± 6 | 88% |
| N-(2,6-dimethylphenyl)-N'-4-pyridinyl urea | 30 μM | 68 ± 6 | 106% |
| | 100 μM | 91 ± 7 | 81% |
| N-(2-chloro-6-methylphenyl)-N'-4-pyridinyl urea | 30 μM | 73 ± 6 | 101% |
| | 100 μM | 92 ± 4 | 80% |
| Carbamazepine | 30 μM | 116 ± 3 | 53% |
| | 100 μM | 78 ± 4 | 95% |

LDH Release Determinations: n = 4 for each mean value.
[a] % Inh refers to the percent inhibition of the release of lactate dehydrogenase in comparison to hypoxic control cultures.

What is claimed is:

1. A method for treating neurodegenerative diseases or disorders which comprises administering to a mammal in need a therapeutically effective amount of a compound selected from ralitoline, phenytoin, lamotrigine, carbamazepine, lidocaine or tetrodotoxin.

2. A method for treating neurodegenerative diseases or disorders as in claim 1 which comprises administering a therapeutically effective amount of ralitoline.

3. A method for treating neurodegenerative diseases or disorders as in claim 1 which comprises administering a therapeutically effective amount of phenytoin.

4. A method for treating neurodegenerative diseases or disorders as in claim 1 which comprises administering a therapeutically effective amount of lamotrigine.

5. A method for treating neurodegenerative diseases or disorders as in claim 1 which comprises administering a therapeutically effective amount of carbamazepine.

6. A method for treating neurodegenerative diseases or disorders as in claim 1 which comprises administering a therapeutically effective amount of lidocaine.

7. A method for treating neurodegenerative diseases or disorders as in claim 1 which comprises administering a therapeutically effective amount of tetrodotoxin.

8. A method for treating neurodegenerative diseases or disorders which comprises administering to a mammal in need a therapeutically effective amount of a compound of formula

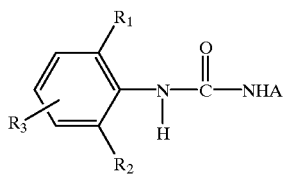

wherein A is 4-pyridinyl; $R_1$ and $R_2$ are independently halogen, lower alkyl, lower alkoxy, or nitro, and $R_3$ is hydrogen, halogen, lower alkyl, lower alkoxy, or nitro, or a pharmaceutically acceptable acid addition salt thereof.

9. A method according to claim 8 wherein the neurodegenerative disorder is acute brain injury.

10. A method according to claim 8 wherein the neurodegenerative disorder is stroke.

11. A method according to claim 8 wherein the neurodegenerative disease is Alzheimer's disease.

12. A method according to claim 8 wherein the neurodegenerative disease is Huntington's disease.

13. A method according to claim 8 wherein the neurodegenerative disease is Amyotrophic Lateral Sclerosis.

14. A method according to claim 8 wherein the neurodegenerative disease is Parkinson's disease.

15. A method according to claim 8 wherein the compound is N-(2-chloro-6-methylphenyl)-N'-4-pyridinyl urea monohydrochloride or a pharmaceutically acceptable salt thereof.

16. A method according to claim 8 wherein the compound is N-(2,3-dichlorophenyl)-N'-4-pyridinyl urea or a pharmaceutically acceptable salt thereof.

17. A method according to claim 8 wherein an individual dose is administered in the range from about 10 mg to about 1000 mg intravenously of the compound or a pharmaceutically acceptable salt thereof is administered.

18. A method according to claim 8 wherein an individual dose is in the range from about 50 mg to about 2000 mg parenterally or about 50 to about 5000 mg enterally of the compound or a pharmaceutically acceptable salt thereof is administered.

* * * * *